US006652533B2

(12) United States Patent
O'Neil

(10) Patent No.: US 6,652,533 B2
(45) Date of Patent: Nov. 25, 2003

(54) MEDICAL INSERTER TOOL WITH SLAPHAMMER

(75) Inventor: Michael J. O'Neil, West Barnstable, MA (US)

(73) Assignee: DePuy Acromed, Inc., Raynham, MA (US)

( * ) Notice: Subject to any disclaimer, the term of this patent is extended or adjusted under 35 U.S.C. 154(b) by 79 days.

(21) Appl. No.: 09/957,331

(22) Filed: Sep. 20, 2001

(65) Prior Publication Data

US 2003/0055434 A1 Mar. 20, 2003

(51) Int. Cl.⁷ ............................................. A61B 17/56
(52) U.S. Cl. ......................... 606/100; 606/99; 606/90; 623/17.11
(58) Field of Search ........................ 606/100, 99, 90, 606/61, 108, 79, 104; 254/98, 100; 623/17.11, 17.16

(56) References Cited

U.S. PATENT DOCUMENTS

| | | | |
|---|---|---|---|
| 3,486,505 A | * 12/1969 | Morrison | ..................... 606/90 |
| 4,034,746 A | 7/1977 | Williams | |
| 4,697,586 A | 10/1987 | Gazale | |
| 4,877,020 A | 10/1989 | Vich | |
| 5,019,081 A | 5/1991 | Watanabe | |
| 5,052,373 A | 10/1991 | Michelson | |
| 5,314,477 A | 5/1994 | Marnay | |
| 5,431,658 A | * 7/1995 | Moskovich | ................... 606/99 |
| 5,476,467 A | * 12/1995 | Benoist | ..................... 606/100 |
| 5,505,732 A | 4/1996 | Michelson | |
| 5,797,909 A | 8/1998 | Michelson | |
| 5,913,860 A | * 6/1999 | Scholl | ........................ 606/100 |
| 5,944,658 A | 8/1999 | Koros et al. | |
| 5,957,927 A | 9/1999 | Magee et al. | |
| 6,063,088 A | 5/2000 | Winslow | |
| 6,096,038 A | 8/2000 | Michelson | |
| RE37,005 E | 12/2000 | Michelson et al. | |
| 6,156,040 A | 12/2000 | Yonemura et al. | |
| 6,159,212 A | 12/2000 | Schoedinger, III et al. | |
| 6,159,244 A | 12/2000 | Suddaby | |
| 6,174,311 B1 | 1/2001 | Branch et al. | |
| 6,197,033 B1 | 3/2001 | Haid, Jr. et al. | |
| 6,478,800 B1 | * 11/2002 | Fraser et al. | ................... 606/99 |

FOREIGN PATENT DOCUMENTS

DE        299 16 078        11/1999

* cited by examiner

*Primary Examiner*—Pedro Philogene
(74) *Attorney, Agent, or Firm*—Nutter, McClennen & Fish LLP

(57) ABSTRACT

An installation tool is provided for the efficient and effective placement of an implant between adjacent bone structures, preferably adjacent vertebral bodies, and for the subsequent removal of the device without displacement of the implant. The installation tool generally includes a pair of opposed levers, a pusher assembly disposed between the levers, and an installation tool removing element having a mass slidably disposed with respect to at least a portion of the pusher assembly. The levers are effective to separate adjacent bone structures, such as adjacent vertebrae, upon insertion of an implant. The pusher assembly is slidably movable with respect to the levers, and is effective to insert an implant between the adjacent bone structures. Once the implant is positioned between the adjacent vertebrae, the mass can be used to apply a proximally directed force to the opposed levers, thereby removing the instrument from the space between the adjacent bone structures.

42 Claims, 11 Drawing Sheets

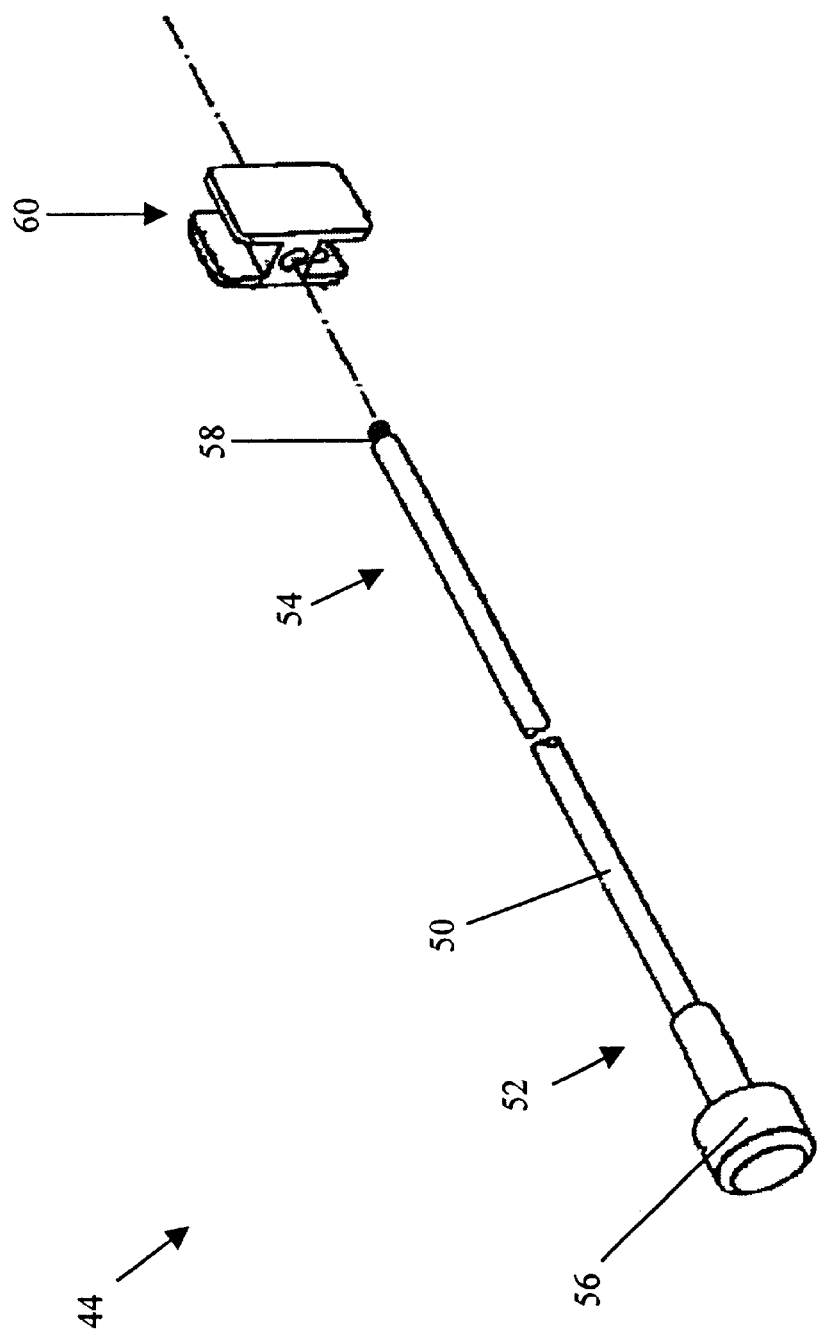

MEDICAL INSERTER TOOL WITH SLAPHAMMER

FIELD OF THE INVENTION

The present invention relates to tools for inserting prostheses within the body, and more particularly to an instrument for inserting an implant between adjacent bone structures, and for subsequently removing the instrument.

BACKGROUND OF THE INVENTION

Degenerative changes in the spine can cause the loss of normal structure and/or function. The intervertebral disc is one structure prone to the degenerative changes associated with wear and tear, aging, and even misuse. Over time the collagen (protein) structure of the intervertebral disc weakens and may become structurally unsound. Additionally, the water and proteoglycan (the molecules that attract water) content decreases, thereby narrowing the space between the adjacent vertebrae, which can result in nerve root compression and pain. These changes can lead to the disc's inability to handle mechanical stress.

One form of treatment available for degenerative disc disease is spinal fusion surgery, which involves the surgical removal of a portion or all of an intervertebral disc followed by fusion of the adjacent vertebrae. A prosthetic device, e.g. a fusion cage, is usually placed between the two adjacent vertebrae to fill the space left by the removed disc and to allow bone to grow between the adjacent vertebrae.

Spinal fusion procedures can present the surgeon with several challenges, especially where the disc is severely degenerative. When the natural disc is removed, the adjacent vertebral bodies collapse upon each other thereby requiring the bodies to be separated to enable placement of the prosthesis. However, separation or distraction of the vertebral bodies beyond a certain degree can result in further injury or damage to the vertebrae. Conversely, where the disc is severely degenerative, the narrow disc space and lack of elasticity between the vertebrae can hinder the surgeon's ability to separate the vertebrae to a height sufficient to enable placement of the prosthesis.

To overcome some of these problems, specialized tools have been developed to facilitate the placement of disc prostheses between adjacent vertebral bodies of a patient's spine. Among the known tools for performing such procedures are spinal distracters, e.g. spreaders, and insertion devices. In general, the spreader is placed between adjacent vertebrae, and then used to pry the vertebrae apart. Once the space between the vertebral bodies is sufficient to enable placement of a prosthesis, the prosthetic device can then be inserted, either manually or with an insertion tool, into the space to hold the adjacent vertebrae apart. Typically, cancellous bone is packed in and/or around the implant to promote fusion of the adjacent vertebrae.

While most spreader devices are effective to assist surgeons with the placement of disc prosthesis, the use of such tools can prove cumbersome. For example, insertion of a spreader device into the limited disc space can cause fracture of a vertebra. Moreover, once inserted, the spreaders can cause over-distraction of the vertebral bodies, or can hinder placement of the prosthesis. In the presence of degenerative disease or chronic changes where the disc space has become narrow, it can be difficult to maintain an adequate interbody height and, at the same time, insert and position the implant. Over-insertion, or under-insertion of the prosthesis can lead to pain, postural problems and/or limited mobility or freedom of movement.

Once the disc is properly positioned between the vertebral bodies, further difficulty can arise in attempting to remove the insertion tool without displacing the disc. Improper placement of the disc can hinder fusion, and/or can result in misalignment of the adjacent vertebrae.

Despite existing tools and technologies, there remains a need for a device to facilitate the safe and accurate insertion of a disc prosthesis between adjacent vertebral bodies, and to subsequently remove the device without displacing the implanted disc.

SUMMARY OF THE INVENTION

The present invention provides an installation tool for inserting an implant, such as an artificial disc, between adjacent bone structures, and for the subsequent removal of the tool without displacement of the implant. In one embodiment, an installation tool is provided having a pair of opposed levers, each lever having a proximal portion and a distal portion. A placement element, such as a pusher assembly, is disposed between the levers and slidably movable between a first, proximal position and a second, distal position. The placement element is effective to insert an implant between adjacent bone structures. The installation tool further includes a mass slidably disposed with respect to at least a portion of the placement element. The mass is effective to be selectively reciprocated to apply a proximally directed force to the opposed levers, thereby removing the installation tool from the space between the adjacent bone structures. The position of the placement element is maintained during reciprocation of the slidable mass, thereby preventing movement of the implant during removal of the installation tool.

The installation tool can include a connecting element, such as a fulcrum, disposed between the opposed levers for allowing movement of the levers with respect to each other. The connecting element can optionally include a force receiving element, such as a cylindrical body, for receiving a force applied by the mass. A groove and engagement element can be provided on the mass and force receiving element for effecting selective movement of the mass with respect to the force receiving element. In one embodiment, movement of the mass between the first and second positions is controlled and limited by a longitudinally extending groove formed in and extending over a portion of the cylindrical body, and an engagement element protruding from a portion of the slidable mass and adapted to mate with the groove. The force receiving element and can optionally include a locking element for locking the mass in a stationary position, preferably the first, distal position.

In one embodiment, the placement element is a pusher assembly having a pusher rod having a proximal end and a distal end. The proximal end can include a handle for facilitating grasping of the pusher rod. The distal end can include an engagement element for mating with a prosthesis. The fulcrum and the cylindrical body each include a bore extending therethrough that is adapted to slidably receive the pusher rod. In a further embodiment, the pusher assembly can include a pusher block mated to the distal end of the pusher rod. The pusher block is adapted to be positioned between the two levers and is selectively moveable between an initial location distal of the fulcrum and a final location adjacent the distal end of the levers.

BRIEF DESCRIPTION OF THE DRAWINGS

The invention will be more fully understood from the following detailed description taken in conjunction with the accompanying drawings, in which:

FIG. 5 is a top perspective view of one embodiment of a pusher assembly according to the present invention;

DETAILED DESCRIPTION OF THE INVENTION

The present invention provides an installation tool that is useful for the efficient and effective placement of a prosthesis between adjacent bone structures, preferably adjacent vertebral bodies, and for the subsequent removal of the device without displacement of the prosthesis. Although the invention is described primarily with reference to use for the installation of a prosthesis or fusion device between adjacent vertebral bodies, it is understood that the installation tool of the invention can be used to place other elements between vertebral bodies, or in other locations within a patient's body. Exemplary elements that can be placed between vertebral bodies include, but are not limited to, interbody cages, fusion devices, spacers, grafts, and the like.

The tool 10 according to the present invention includes a first portion that is effective to insert a prosthesis between adjacent bone structures and a second portion, integrated with the first portion, that is effective to remove the installation portion from between the bone structures after insertion of the prosthesis. The second portion is commonly referred to as a slaphammer.

The installation portion of tool 10 is described with reference to an exemplary embodiment. A person having ordinary skill in the art will appreciate that the slaphammer portion can be used with virtually any installation tool having any configuration.

Figure 1:
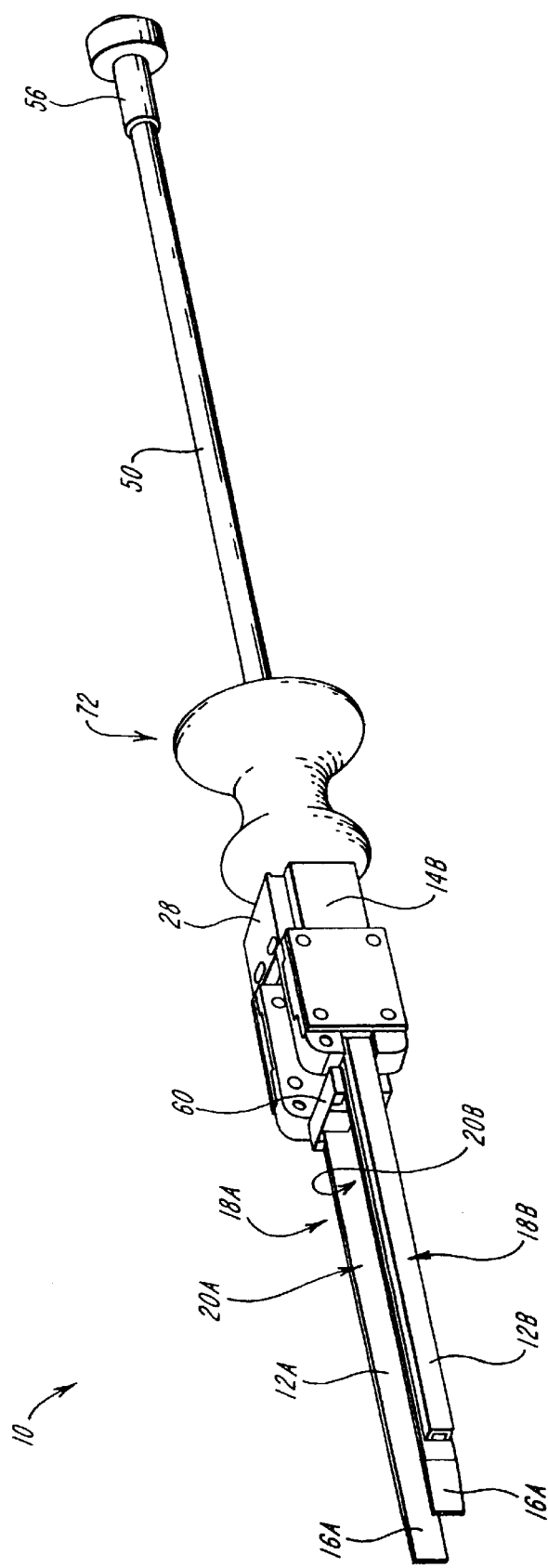
FIG. 1 is a perspective view of an implant installation tool having opposed levers, a pusher assembly, and an installation tool removing element.
Figure 2:
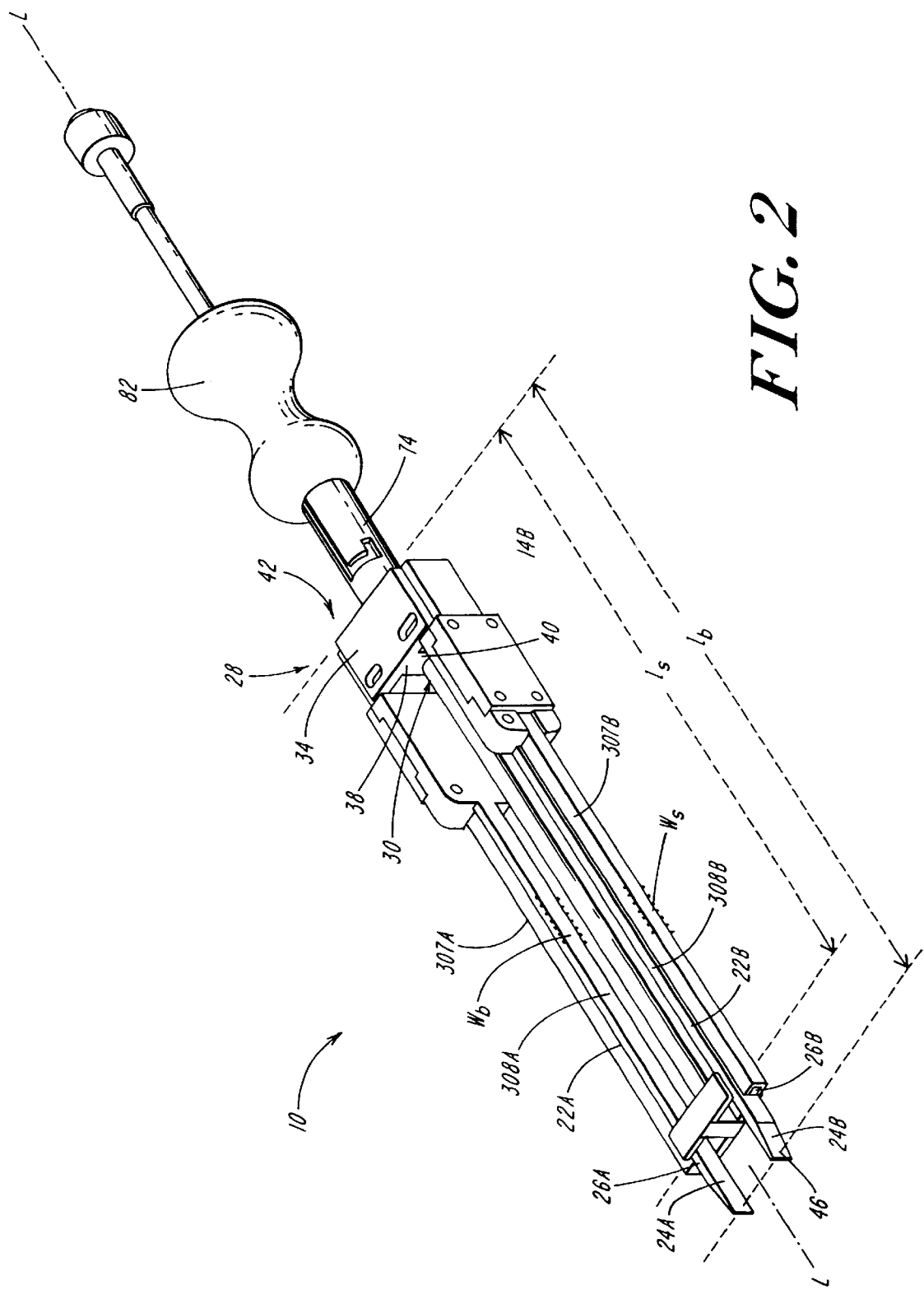
FIG. 2 is a perspective view of the implant installation tool of FIG. 1.

As shown in FIGS. 1, 2, and 5, the installation portion of tool 10 generally includes a pair of opposed levers 12A, 12B, and a placement element 44 disposed between the levers 12A, 12B. In an exemplary embodiment, the placement element 44 is a pusher assembly. The levers 12A, 12B can be movably or pivotally mated to each other, and are effective to separate adjacent bone structures, such as adjacent vertebrae. A connecting element 28 can be disposed between the proximal portion of the levers 12A, 12B for allowing movement of the levers 12A, 12B with respect to each other. The pusher assembly 44, which is effective to insert a prosthesis between the adjacent bone structures, includes a pusher rod 50 slidably movable with respect to the levers. The pusher assembly 44 can optionally include a pusher block 60 mated to the distal end of the pusher rod 50. The slaphammer portion of tool 10 generally includes a slidable mass 82 that is effective to apply a proximally directed force to the opposed levers, thereby facilitating removal of the instrument 10 from the space between the adjacent bone structures. The slaphammer portion can be adapted to apply the force directly to the levers 12A, 12B and/or the connecting element 28 or, alternatively, the tool 10 can include a force receiving element 74 (FIG. 2) adapted to receive the force applied by the slidable mass 82.

The opposed levers 12A, 12B of the installation portion of the tool 10 can have a variety of shapes and sizes, but are preferably elongate members that are mirror images of each other. Each lever 12A, 12B includes a proximal portion 14A, 14B, a distal portion 16A, 16B, an outwardly facing surface 18A, 18B, and an inwardly facing surface 20A, 20B. In an exemplary 10 embodiment, shown in FIGS. 1, 2, and 3, the outwardly and inwardly facing surfaces 18A, 18B, 20A, 20B of each lever 12A, 12B are formed from two separate components, a stop member component 307A, 307B and a blade member component 308A, 308B, which are longitudinally separable from one another.

While two components are shown to form the levers 12A, 12B, a person having ordinary skill in the art will appreciate that each lever 12A, 12B can be formed from a single elongate member having some or all of the features disclosed herein. Moreover, while one of the components is referred to as a "stop member component," a person having ordinary skill in the art will appreciate that the stop member component does not need to function as a stop member.

The blade member component 308A, 308B forms the inwardly facing portion 20A, 20B of each lever 12A, 12B and includes a blade tip 24A, 24B to facilitate the placement of the levers 12A, 12B between adjacent bone structures. The outwardly facing surface 18A, 18B of each blade tip 24A, 24B can include a beveled or radiused surface 46 to further facilitate insertion of the levers 12A, 12B between the vertebral bodies. The inwardly facing surface of each blade member component 308A, 308B can be adapted to slidably receive a prosthesis during an installation procedure. As shown in FIG. 2, the inwardly facing surfaces 20A, 20B are substantially flattened to enable a prostheses to slide along these surfaces during installation. Alternatively, the inwardly facing surfaces 20A, 20B of the levers 12A, 12B can adapted to receive prosthesis having various shapes and sizes, and they can be modified to have surface features that are complementary to surface features that may be present on a prosthesis to be implanted.

The blade member component 308A, 308B of each lever 12A, 12B can also be adapted to slidably receive a portion of the pusher assembly 44. By way of non-limiting example, each lever 12A, 12B can include a rail 22A, 22B formed on one or more edges of the inwardly facing surface 20A, 20B. The rail 22A, 22B is preferably formed by a portion which extends beyond the width of each lever 12A, 12B. In an exemplary embodiment, the blade member component 308A, 308B has a width $W_b$ greater than the width $W_s$ of the stop member component 307A, 307B, thereby forming the rail 22A, 22B. The pusher block 60 of the pusher assembly 44, which will be described in more detail with reference to FIG. 5, can include a corresponding recess for receiving the rail 22A, 22B. A person having ordinary skill in the art will appreciate that a variety of different mating elements can be provided for slidably mating the pusher block 60 and the levers 12A, 12B.

The stop member component 307, which forms the outwardly facing portion 18A, 18B of each lever 12A, 12B, can include a distal end having a stop surface 26A, 26B. Each stop surface 26A, 26B, which is substantially vertically oriented and distally facing, is adapted to abut a bone structure, such as a vertebral body, during a surgical procedure for installing of a prosthesis between adjacent bone structures. The length $l_b$ of the blade member component 308 should be greater than the length $l_s$ of the stop member component 307 to allow the blade tips 24A, 24B to be inserted between adjacent bone structures, and the stop surface 26A, 26B to abut the exterior sides of the adjacent bone structures. A person having ordinary skill in the art will appreciate that a variety of alternative embodiments can be used to form the stop surface 26A, 26B. For example, the distal end 26A, 26B of each lever can include a protruding member extending outwardly in a direction perpendicular to the longitudinal axis L of the instrument 10.

Figure 3:
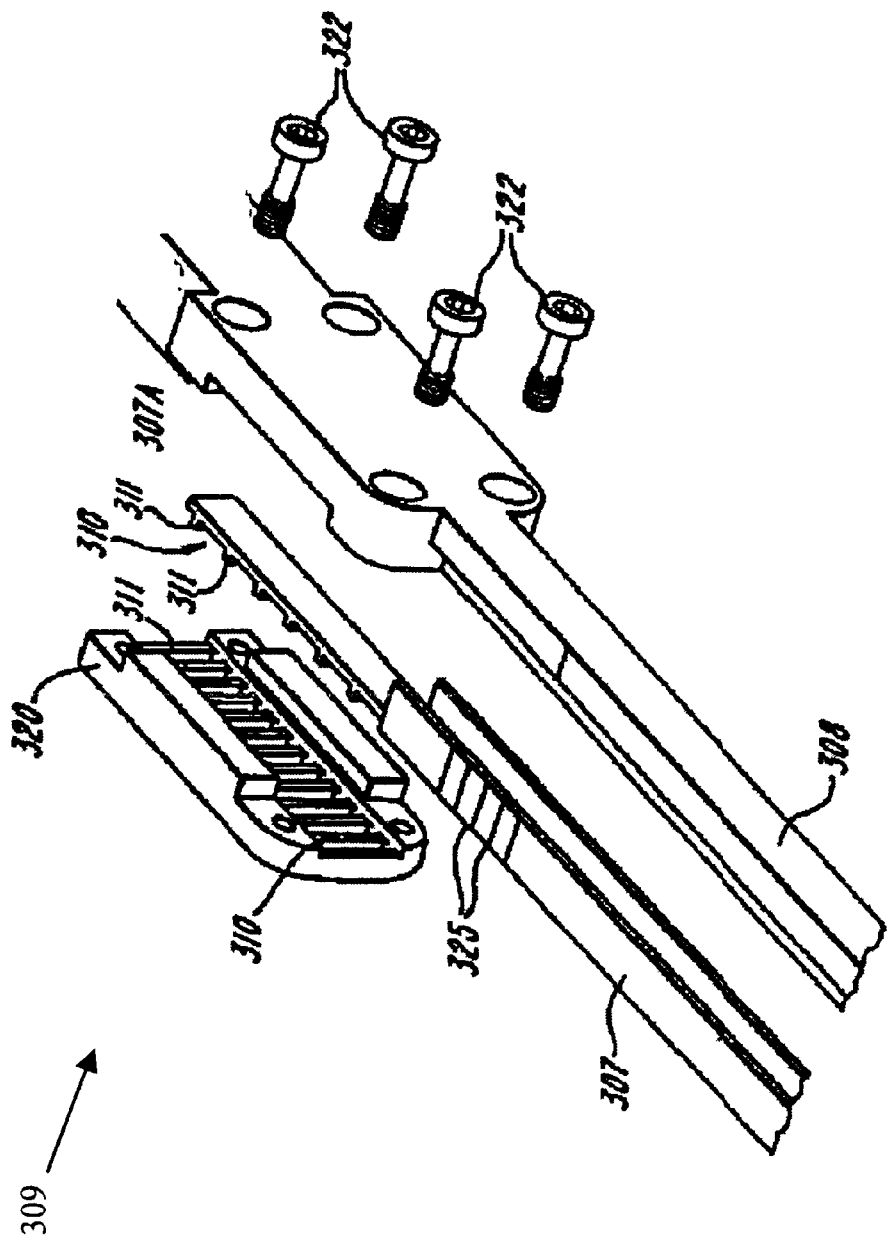
FIG. 3 is an exploded view of a proximal portion of the opposed levers shown in FIG. 1.
Figure 4A:
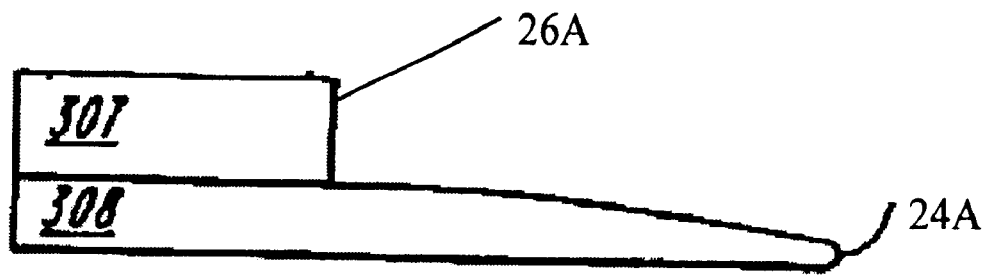
FIG. 4A is a side illustration of the distal portion of one of the opposed levers shown in FIG. 1 having a first length.
Figure 4B:
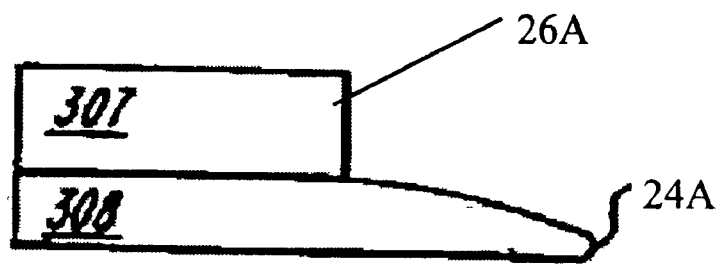
FIG. 4B is another side illustration of the distal portion of one of the opposed levers shown in FIG. 1 having a second length.

The tool 10 can include a feature for permitting selective adjustment of the blade tip length (i.e., the distance between the distal end of blade tips 24A, 24B and stop surface 26A, 26B). As shown in FIG. 3, the tool 10 can include a junction box 309 which houses and secures components 307 and 308. A proximal portion of the stop member component 307, which mates with the inner surface of the cover 320 of the junction box 309, includes a series of grooves 310 separated by raised ridges 311. Similarly, the abutting, inner surface of the cover 320 of the junction box 309 includes grooves and ridges 310, 311 as well. As further illustrated, the cover 320 is secured to levers 12A, 12B by suitable fasteners, such as screws 322. Biasing elements, such as compression springs (not shown) are preferably used to bias the junction box to a position such that the grooves and ridges 310, 311 of the cover 320 and the stop member component 307 mate with and remain firmly secured to one another. Suitable indicia 325 may be present on the stop member component 307 to indicated the position of the stop member component 307 with respect to the blade member component 308. Although FIG. 3 only illustrates the configuration of one of the levers, it is understood that the same construction can be used for both levers. The result of the selective adjustability of the levers 12A, 12B is shown in FIGS. 4A and 4B, in which the length of the blade tip 24A is greater in FIG. 4A than in FIG. 4B.

While the length of the levers 12A, 12B can vary, the length $l_b$ of each blade member component 308A, 308B is preferably between about 200 and 400 mm, and the length $l_s$ of each stop member component 307A, 307B is preferably about 20 mm less than the length of each blade member component 308A, 308B. The width of the levers 12A, 12B can also vary depending on the intended use, but preferably the width $W_b$ of each blade member component 308A, 308B is between about 5 and 10 mm, and the width $W_s$ of each stop member component 307A, 307B is about 4 mm less than the width $W_b$ of each blade member component 308A, 308B.

The proximal portion 14A, 14B of each lever 12A, 12B can be mated by a connecting element, such as a fulcrum 28, which allows relative movement of the levers 12A, 12B in a pivoting manner. The levers 12A, 12B are movable between an open position, as shown in FIG. 1, and a closed position (not shown) wherein the distal portions 16A, 16B of each lever 12A, 12B are in physical contact with each other. Referring back to FIG. 2, the fulcrum 28 is disposed between the proximal portion 14A, 14B of each lever 12A, 12B, and is substantially a block-like object having a central bore 30 extending longitudinally therethrough. While there is no absolute top or bottom of the tool 10, for ease of reference the fulcrum 28 and other components of the tool 10 will be described herein with reference to the illustrated orientation.

As shown, the fulcrum 28 includes a top surface 34, a bottom surface 36, a core section 38 having a distal end surface 40 and a proximal end surface 42, and opposed recesses 48 (not shown) defined by the top and bottom surfaces 34, 36. The core section 38 of the fulcrum 28 preferably includes a central bore 30 extending between the distal end surface 40 and the proximal end surface 42. The bore 30 is adapted to slidably receive a portion of the pusher assembly 44. The opposed recesses 48 are adapted to seat the proximal ends 14A, 14B of the opposed levers 12A, 12B. In an exemplary embodiment, the fulcrum 28 includes a biasing element (not shown), such as a coil or spring, disposed within each recess 48 and adapted to provide movement of the proximal end 14A, 14B of the levers 12A, 12B with respect to each other and with respect to the fulcrum 28.

A person having ordinary skill in the art will appreciate that the fulcrum 28 may assume virtually any size and shape that is able to render it effective to separate the proximal portion 14A, 14B of the levers 12A, 12B, while allowing the distal portion 16A, 16B of the levers 12A, 12B to be moved between the open and closed positions.

Referring to FIG. 5, the tool 10 further includes a placement element slidably disposed with respect to the fulcrum 28 and the levers 12A, 12B, and adapted to insert a prosthesis between adjacent bone structures. A person having ordinary skill in the art will appreciate that the placement element can have a variety of different structures and can employ a variety of different mechanisms for inserting or otherwise placing an implant between adjacent bone structures. By way of non-limiting example, the placement element 44 can be include a trigger actuated plunger that pushes against a piston to insert the implant between adjacent bone structures. Other types of placement elements 44 can include, for example, those which employ a threaded advancement mechanism, a pulley assembly, or a spring mechanism for inserting an implant between adjacent bone structures.

In an exemplary embodiment, the placement element is a pusher assembly 44 including a pusher rod 50 having a proximal end 52 and a distal end 54, and, optionally, a pusher block 60 mated to the distal end 54 of the pusher rod 50. The pusher assembly 18 is slidably movable between a first, proximal position shown in FIG. 1, and a second, distal position shown in FIG. 2.

The pusher rod 50 is utilized to actuate the pusher block 60, and is preferably an elongate, cylindrical member. The proximal end 52 can include a gripping element, such as a handle 56 to facilitate grasping of the pusher assembly 44. The distal end 54 of the pusher rod 50 preferably includes a threaded region 58 for connecting the pusher rod 50 to the pusher block 60. The rod 50 is adapted to be positioned between the levers 12A, 12B such that it extends through the central bore 30 in the fulcrum 28, as shown in FIG. 2. The threaded region 58 of the rod 50 mates with a threaded blind bore 70 formed in the pusher block 60. In this way, the rod 50 positively engages the pusher block 60 so that forward and rearward movement of the pusher rod 50 will directly move the pusher block 60. In an alternative embodiment, the distal end 54 of the pusher rod 50 can be adapted to engage or abut the proximal surface of a prosthesis to be implanted. For example, the threaded region 58 of the rod 50 can mate with a threaded blind bore formed in the prosthesis (not shown).

Figure 6:
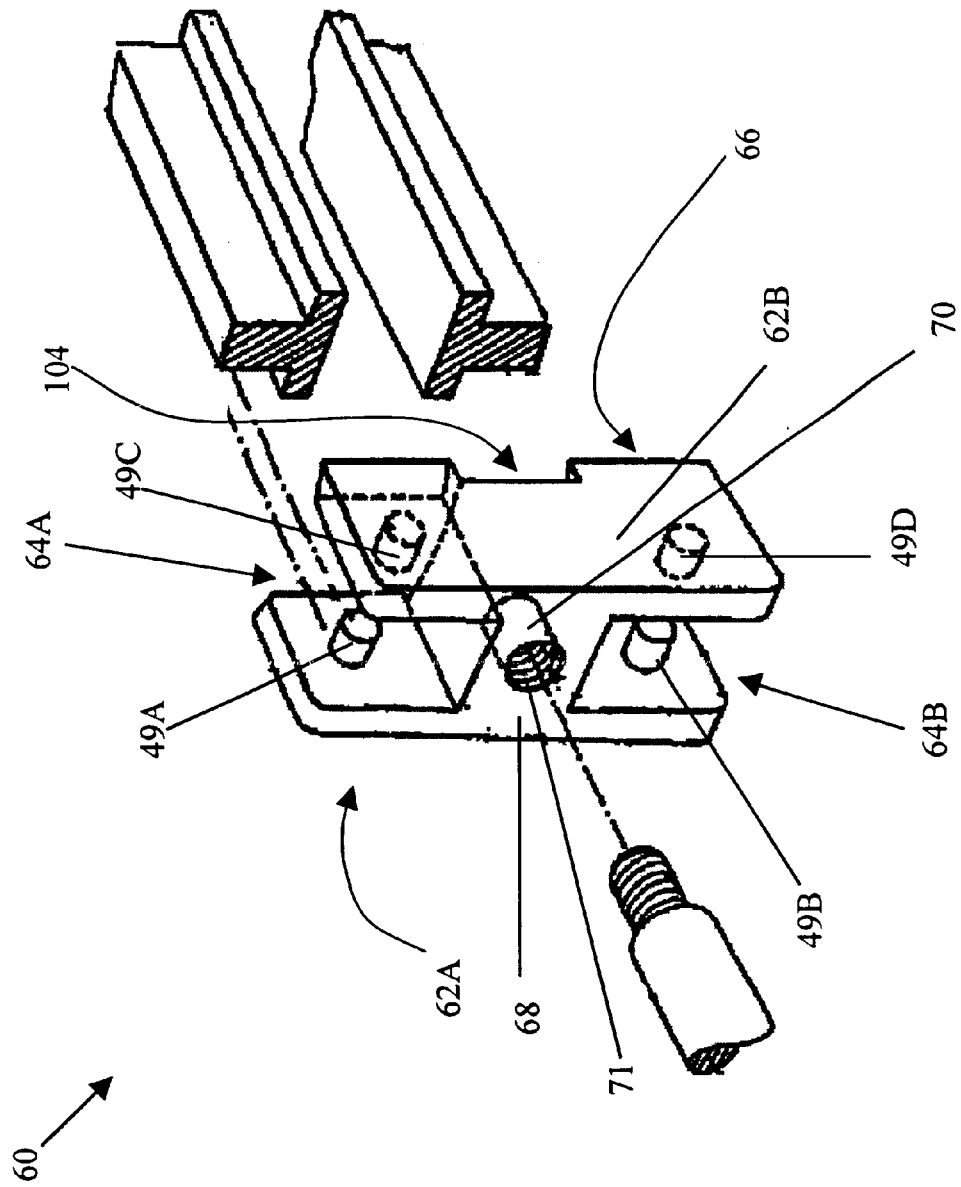
FIG. 6 is an exploded view of the pusher assembly shown in FIG. 5, with a portion of the levers.

Pusher block 60, shown in more detail in FIG. 6, may be in the form of a substantially block-like object having side walls 62A, 62B that define opposed recesses 64A, 64B. The inwardly facing portion of each side wall 62A, 62B can include a guide post 49A, 49B, 49C, 49D that extends into the recess 64A, 64B for mating the pusher block 60 with the levers 12A, 12B. When mated, the rails 22A, 22B of each lever 12A, 12B extend between the guide posts 49 and the inner-most wall of each recess 64A, 64B, thereby preventing the levers 12A, 12B from separating. The proximally facing wall (not shown) of the pusher block 60 may include a blind bore 70 having internal threads 71 adapted to mate with complimentary threads 58 formed on a distal end 54 of the pusher rod 50.

The distally facing wall 66 of the pusher block 60 can include a recessed region 104 that is adapted to nest a prosthesis (not shown). As illustrated in FIG. 8B, the recessed region 104 has dimensions that enable a prosthesis, e.g. an artificial disc 204, to fit loosely therein. One of ordinary skill in the art will appreciate that the recessed area 104 should have dimensions slightly greater than the dimensions of the prosthesis 204 so as to avoid a frictional fit that may inhibit free release of the prosthesis from the tool.

One of ordinary skill in the art will appreciate that the pusher block may assume a variety of sizes and geometries that facilitate engagement with a variety of different prostheses.

Referring back to FIGS. 1 and 2, the tool 10 further includes an integrated slaphammer portion 72 for removing the tool 10 after a prosthesis is positioned between adjacent bone structures. As previously stated, the slaphammer portion of tool 10 can be used with virtually any type of installation tool, and is not limited to the installation portion of tool 10 described herein.

Figure 7A:
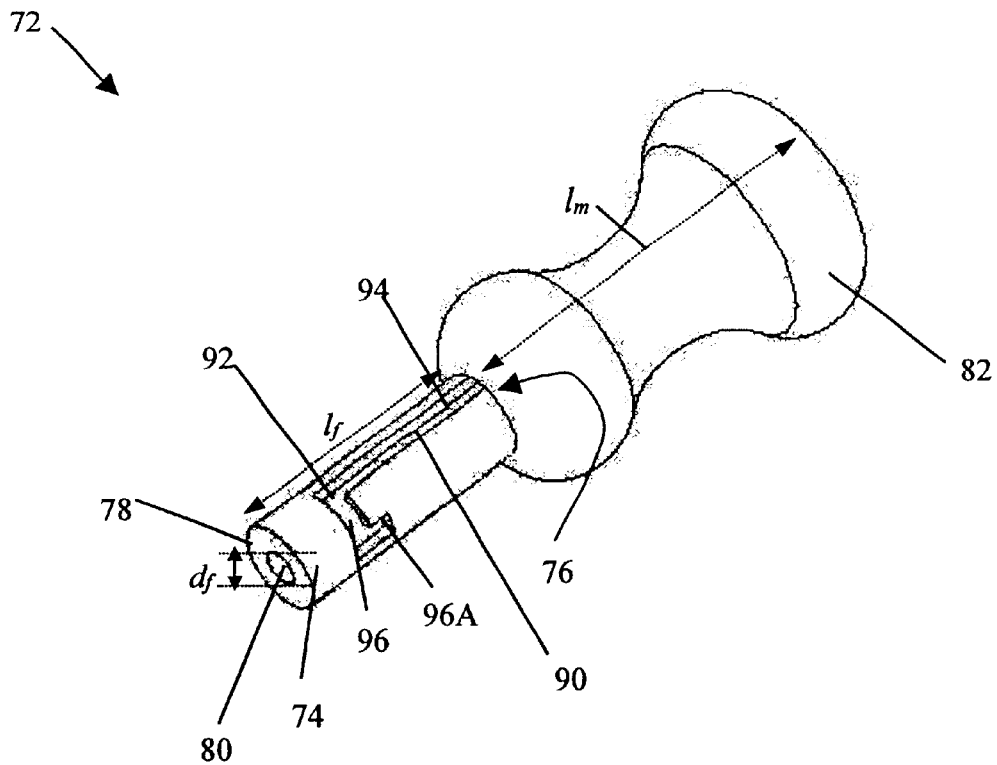
FIG. 7A is a perspective view of the installation tool removing element shown in FIG. 1.

As shown in more detail in FIG. 7A, the slaphammer 72 includes a slidable mass 82 and, optionally, a force receiving element 74. The force receiving element 74 can have any shape or size, and can be formed integrally with or mated to the fulcrum 28 and/or the levers 12A, 12B. In an exemplary embodiment, the force receiving element 74 is in the shape of a cylindrical body having a proximal end 76, a distal end 78, and a central bore 80 extending therethrough. The distal end 78 is adhesively or mechanically mated to the proximal end surface 42 of the fulcrum 28 (FIG. 2).

The force receiving element 74 can have any length $l_f$, but should have a length $l_f$ sufficient to allow slidable movement of the mass 82 with respect to the force receiving element 74. Moreover, the length $l_f$ should be sufficient to allow a force to be applied by the mass 82 to the force receiving element 74 to move the force receiving element 74 in a proximal direction. Preferably, the length $l_f$ is between about 50 and 100 mm. The diameter $d_f$ of the central bore 80 in the cylindrical body 74 should be sufficient to allow slidable movement of the pusher rod 50 therethrough, and is preferably between about 5 and 10 mm.

Figure 7B:
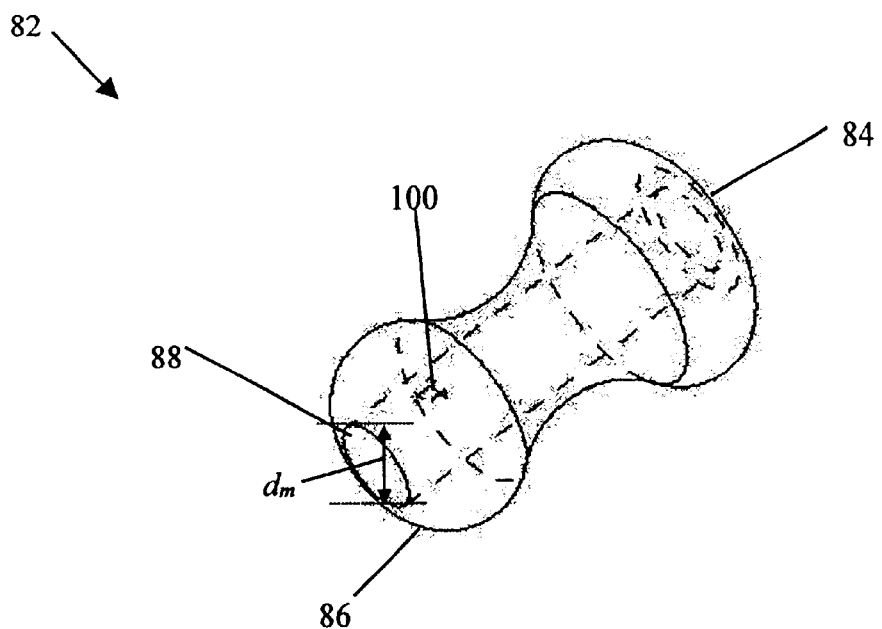
FIG. 7B is a perspective view of the slidable mass shown in FIG. 7A.

The mass 82, shown in FIG. 7B, includes a proximal end 84, a distal end 86, and a central bore or lumen 88 extending therebetween and adapted to receive the force receiving element 74. The mass 82 is slidably disposed around the force receiving element 74 and movable between a first, proximal position (shown in FIGS. 2 and 7A), and a second, distal position (shown in FIG. 1). The mass 82 can have any shape and size, but is preferably generally cylindrical and has a shape adapted to facilitate grasping of the mass 82 to effect movement between the first and second positions.

The mass 82 should have a length $l_m$ substantially the same as the length $l_f$ of the force receiving element 74, and preferably has a length $l_m$ between about 50 and 100 mm. The central bore or lumen 88 of the mass 82 should have a diameter $d_m$ greater than the diameter $d_f$ of the central bore 80. Preferably, the diameter $d_m$ is adapted to allow slidable movement of the mass 82 with respect to the force receiving element 74, and is preferably between about 6 and 11 mm. The mass 82 can have any weight, but preferably has a weight between about 2 and 10 kg.

While FIGS. 1, 2, 7A, and 7B illustrate the mass 82 slidably mated to the force receiving element 74, a person having ordinary skill in the art will appreciate that a variety of different embodiments can be used to form the slaphammer 72. For example, the fulcrum 28 and/or the levers 12A, 12B can form the force receiving element 74, and a mass can be slidably mated directly to the fulcrum 28 and/or levers 12A, 12B.

As illustrated in FIG. 7A, the slaphammer 72 can include an engagement member disposed between the force receiving element 74 and the slidable mass 82 for limiting movement of the mass 82 with respect to the force receiving element 74. While a variety of different engagement members can be used, the engagement member is preferably an elongate track or groove formed in or on one of the mass 82 and the force receiving element 74, and a corresponding protruding member formed in or on the other one of the mass 82 and the force receiving element 74. The protruding member is adapted to mate with the groove to effect selective movement of the mass 82 with respect to the force receiving element 74.

In an exemplary embodiment, the groove 90 is formed in the force receiving element 74 and extends parallel to the longitudinal axis L of the instrument 10. The groove 90 preferably extends along a substantial portion of the force receiving element 74 and includes a proximal end 94 and a distal end 92. A corresponding protruding member, shown in FIG. 7B, is disposed within the central lumen 88 of the slidable mass 82 and is adapted to be slidably disposed within the groove 90. The protruding member 100, e.g. a pin member, should be positioned to radially extend within the lumen 88 of the slidable mass 82 such that the protruding member 100 extends into the groove 90 when the mass 82 is slidably disposed around the force receiving element 74. Thus, in use the groove 90 is effective to limit movement of the mass 82 between the proximal position (FIG. 1) and the distal position (FIG. 2). Moreover, the proximal end 94 of the groove 90 is adapted to receive a force applied by the mass 82. The force is the result of the protruding member 100 impacting the proximal end surface 94 of the groove 90 each time the mass 82 is moved proximally.

The slaphammer 72 can optionally include a locking feature for preventing movement of the mass 82 with respect to the force receiving element 74. While a variety of different locking features can be provided, an exemplary locking feature 96 (shown in FIG. 7A) is a substantially L-shaped groove 96 extending radially around a portion of the force receiving element 74 and in communication with the distal end 92 of the groove 90. In use, the slidable mass 82 is rotated in the first distal position (FIG. 1), and then moved proximally to position the pin member 100 within the locking feature 96, thereby preventing movement of the mass 82 to the second distal position (FIG. 2). The proximally-directed portion 96A of the L-shaped groove 96 can include a positive engagement feature adapted to bias or engage the pin member 100. The mass 82 is moved distally and rotated in the opposite direction to remove the mass 82 from the locked position. A person having ordinary skill in the art will readily appreciate that a variety of different locking elements can be provided for preventing movement of the mass 82 with respect to the force receiving element 74.

Figure 8A:
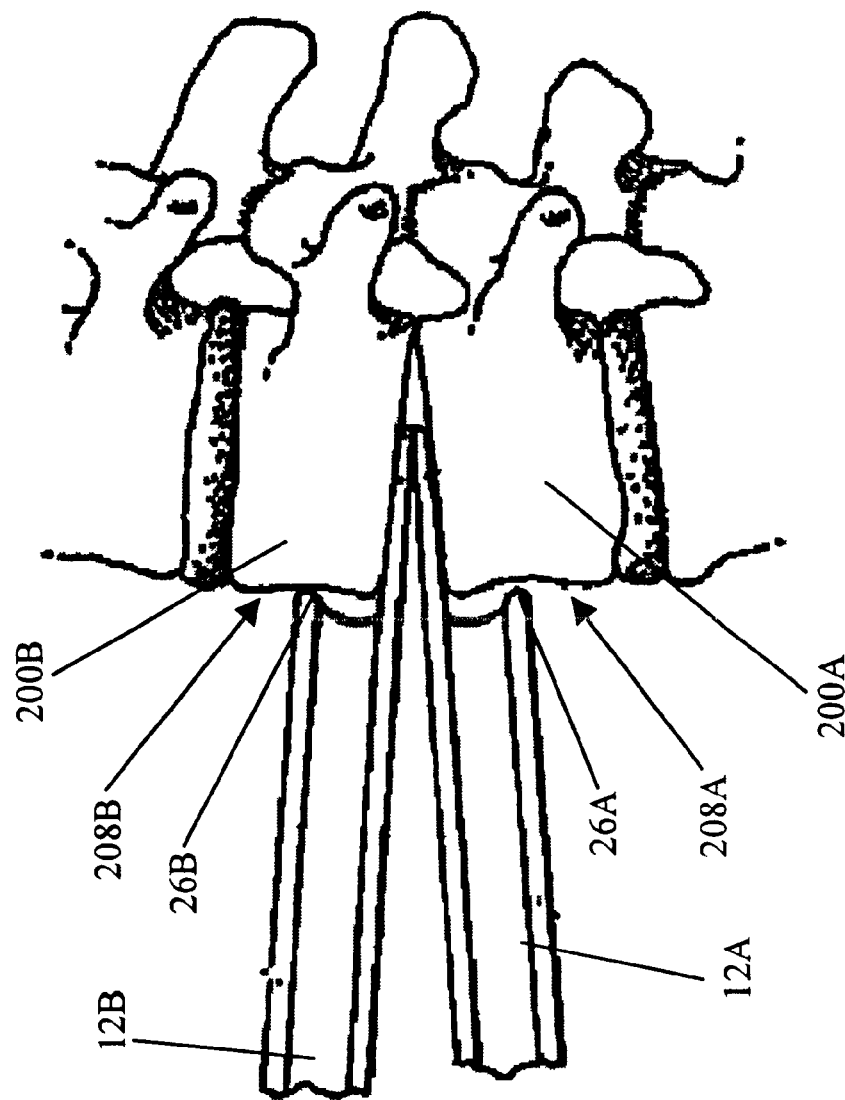
FIGS. 8A–8D illustrate, sequentially, the operation of the implant installation tool according to the present invention during the installation of a prosthesis component.
Figure 8B:
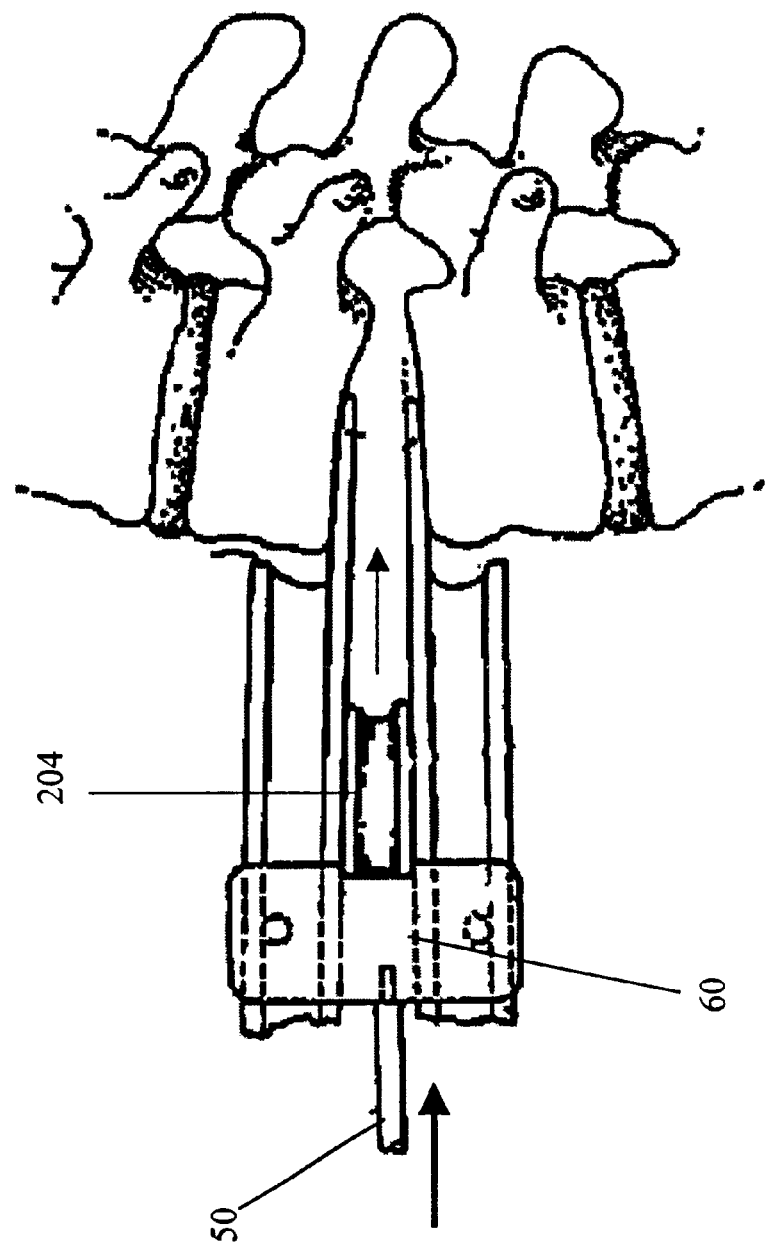

FIGS. 1 and 8A–8D sequentially illustrate the use of tool 10 for the installation of a prosthesis 204. The tool is first assembled, as shown in FIG. 1, with the pusher assembly 44 positioned in the proximal position and the slidable mass 82 positioned in the distal, locked position. The prosthesis 204 is placed against the distal end surface 66 of the pusher block 60 between the levers 12A, 12B. With the blade tips 24A, 24B in the closed position, as shown in FIG. 8A, the blade tips 24A, 24B are wedged between adjacent vertebral bodies 200A, 200B to effect slight separation between the vertebrae. The blade tips 24A, 24B should be fully inserted between the vertebral bodies 200A, 200B, as shown in FIG. 8A, so as to enable the stop surface 26A, 26B of each lever 12A, 12B to abut the posterior side 208A, 208B of the vertebral bodies 200A, 200B.

Figure 8C:
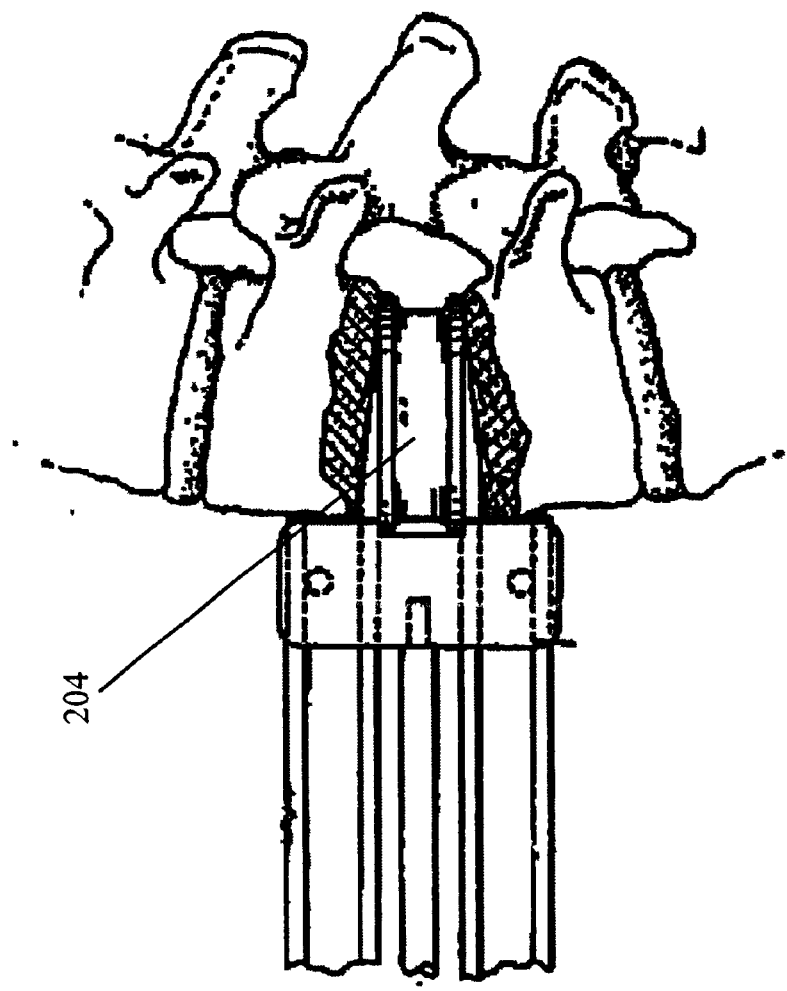
Figure 8D:
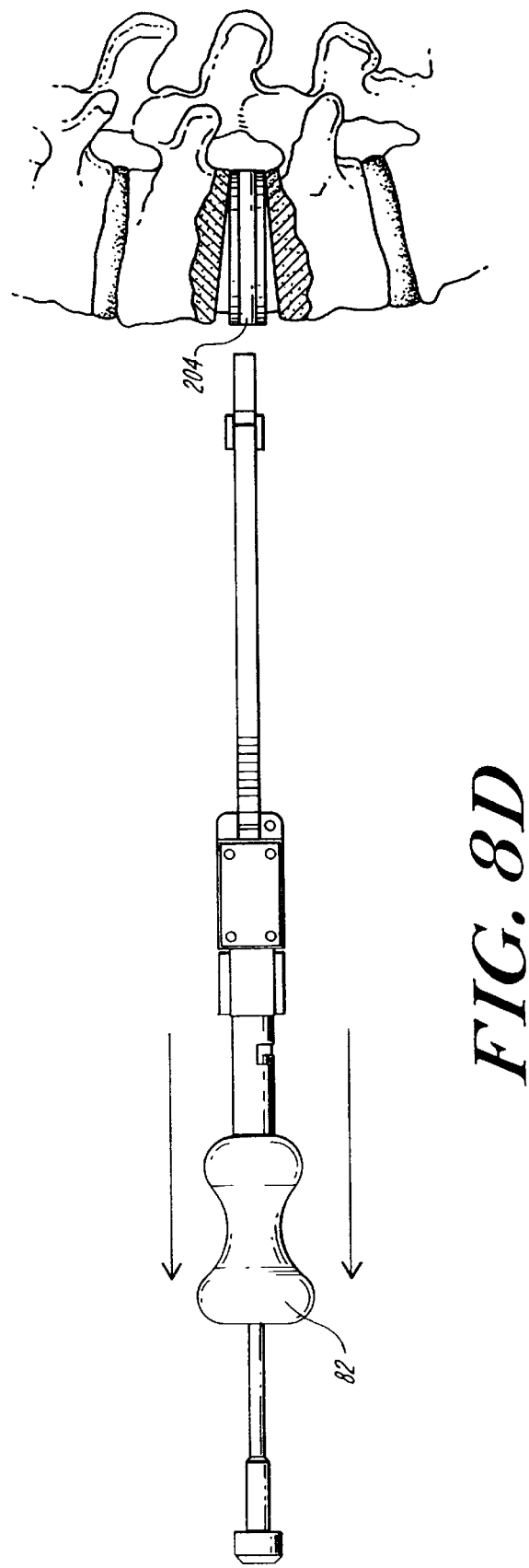

As shown in FIG. 8B, the pusher rod 50 is then advanced forward, causing distal movement of the pusher block 60 and artificial prosthesis 204. The forward or distal movement of pusher block 60 and the artificial prosthesis 204 also causes further separation of the blade tips 24A, 24B and thus further separation of the vertebral bodies 200A, 200B. Advancement of the pusher block 60 and the artificial prosthesis 204 continues until, as shown in FIG. 8C, the prosthesis 204 is properly installed between the adjacent vertebral bodies 200A, 200B. FIGS. 8B and 8C illustrate that at all times separation of the vertebral bodies is only effected to the extent necessary to insert the prosthesis 204. Excessive distraction or separation of the vertebral bodies does not occur because the separation of vertical bodies is caused by the prosthesis and is controlled by the prosthesis thickness dimensions.

Once the prosthesis 204 is implanted between the adjacent vertebrae 200A, 200B, the slidable mass 82 is rotated to remove the mass 82 from the locked position. While the pusher assembly 44 is held against the prosthesis 204 and the adjacent vertebrae 200A, 200B (FIGS. 8B and 8C), the mass 82 is selectively reciprocated to apply a proximally directed force to the force receiving element 74, thereby applying a proximally directed force to the fulcrum 28 and the opposed levers 12A, 12B. The force is a result of the protruding member 100 impacting the proximal end surface 94 of the groove 90 each time the mass 82 is moved proximally. Movement of the mass 82 is effected until the levers 12A, 12B are removed from the vertebral space.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implant installation tool, comprising:
   a pair of opposed levers, each having a proximal portion and a distal portion;
   a placement element disposed between the levers and effective to insert an implant between adjacent bone structures;
   a mass slidably disposed with respect to at least a portion of the placement element and effective to be selectively reciprocated to apply a proximally directed force to the opposed levers.

2. The implant installation tool of claim 1, wherein the placement element comprises a pusher assembly disposed between the levers and slidably movable between a first, proximal position and a second, distal position.

3. The implant installation tool of claim 2, further comprising a connecting element disposed between the opposed levers for allowing pivotal movement of the levers with respect to each other.

4. The implant installation tool of claim 3, further comprising a force receiving element mated to the connecting element for receiving the force applied by the mass.

5. The implant installation tool of claim 4, wherein the mass is slidably mated to the force receiving element.

6. The implant installation tool of claim 5, wherein the force receiving element comprises a cylindrical body, and the mass includes an inner lumen adapted to receive the cylindrical body.

7. The implant installation tool of claim 6, wherein the connecting element includes a distal end and a proximal end, the opposed levers extending distally from the distal end of the connecting element and the cylindrical body extending proximally from the proximal end of the connecting element.

8. The implant installation tool of claim 6, wherein a distal end of the cylindrical body is mated to the connecting element and wherein the cylindrical body further includes an elongate track that extends parallel to a longitudinal axis of the cylindrical body, the elongate track including a locking groove formed at the distal end thereof.

9. The implant installation tool of claim 8, further comprising an engagement element protruding from an inner surface of the mass, the engagement element being effective to mate within the elongate track to effect selective movement of the mass with respect to the cylindrical body.

10. The implant installation tool of claim 6, wherein a distal end of the cylindrical body is mated to the connecting element and wherein the mass further includes an elongate track that extends parallel to a longitudinal axis of the mass, the elongate track including a locking groove formed at the distal end thereof.

11. The implant installation tool of claim 10, further comprising an engagement element protruding from an outer surface of the cylindrical member, the engagement element being effective to mate within the elongate track to effect selective movement of the mass with respect to the cylindrical body.

12. The implant installation tool of claim 6, wherein the mass can be locked into a stationary position.

13. The implant installation tool of claim 8, wherein the pusher assembly comprises an elongate rod having a proximal end and a distal end.

14. The implant installation tool of claim 13, further comprising a pusher block mated to the distal end of the rod such that the pusher block is disposed between the opposed levers.

15. The implant installation tool of claim 13, wherein the connecting element and the cylindrical body include a bore extending therethrough, the pusher rod being slidably disposed within the bore.

16. A medical installation tool, comprising:
    an elongate body having a proximal portion and a distal portion, the distal portion having a member movable with respect to the elongate body and effective to selectively retain a prosthesis and selectively deploy the prosthesis between adjacent bone structures; and
    a mass slidably mated to the elongate body, the mass being selectively moveable with respect to the elongate body such that it is effective to apply a proximally directed force to the elongate body.

17. The installation tool of claim 16, wherein the elongate body comprises a pair of opposed levers and a pusher rod slidably disposed between the opposed levers and having a distal end and a proximal end, the pusher rod and opposed levers being effective to selectively retain a prosthesis, and the pusher rod being effective to selectively deploy the prosthesis between adjacent bone structures.

18. The installation tool of claim 17, further comprising a fulcrum disposed between the opposed levers for allowing pivotal movement of the levers with respect to each other.

19. The installation tool of claim 18, wherein the mass is disposed around a portion of the proximal end of the pusher rod.

20. The installation tool of claim 19, further comprising:
    a substantially cylindrical body mated to and extending proximally from the fulcrum, the slidable mass being slidably mated to the substantially cylindrical body.

21. The installation tool of claim 20, wherein the mass is movable between a first distal position and a second proximal position, and wherein movement of the mass from the first distal position to the second proximal position is effective to apply the force to the tool, the force being sufficient to move the opposed levers and fulcrum proximally with respect to the pusher block and pusher rod.

22. The installation tool of claim 21, wherein the mass can be locked in the first distal position.

23. The installation tool of claim 21, wherein the fulcrum and the cylindrical body each include a bore extending therethrough and adapted to slidably receive the pusher rod.

24. The installation tool of claim 23, further comprising a longitudinally extending groove formed in and extending over a portion of the cylindrical body, and an engaging element protruding from a portion of the slidable mass and adapted to mate within the groove, the mating of the groove and the engaging element being effect to limit movement of the slidable mass between the first and second positions.

25. The installation tool of claim 24, further comprising a locking element for locking the slidable mass in the first distal position.

26. The installation tool of claim 23, further comprising a pusher block mated to the distal end of the rod and positioned between the two levers, the pusher block being selectively moveable between an initial location distal of the fulcrum and a final location adjacent the distal end of the levers.

27. The installation tool of claim 26, wherein the pusher block includes upper and lower recesses, each recess being adapted to seat one of the levers.

28. The installation tool of claim 27, wherein the pusher block includes an implant seating region adapted to receive an implant.

29. The installation tool of claim 28, wherein the pusher block is movable between an initial position and a final position, and wherein the pusher block is effective to separate the levers when advanced from the initial position to the final position.

30. An implant insertion tool, comprising:
    a body having a central bore extending therethrough and a pair of opposed elongate levers extending distally therefrom;
    a pusher rod positioned between the levers; and
    a slidable weight having an inner lumen formed therein and being slidably mated to a portion of the body, the slidable weight being adapted to impact a proximal portion of the tool when moved proximally, thus creating a proximally directed force that acts on the tool.

31. The implant insertion tool of claim 30, wherein the pusher rod is positioned between the levers and slidably extending through the bore of the body, the pusher rod have a proximal end and a distal end.

32. The implant insertion tool of claim 31, further comprising a pusher block mated to the distal end of the pusher rod and disposed between the levers.

33. The implant insertion tool of claim 32, further comprising a substantially cylindrical member extending proximally from the body and having a proximal end and a distal end, the slidable weight being disposed around the cylindrical member.

34. The implant insertion tool of claim 33, wherein the slidable weight is movable between a first position, in which the slidable weight is fully disposed over the cylindrical member, and a second position, in which the slidable weight extends proximally from the proximal end of the cylindrical member.

35. The implant insertion tool of claim 33, wherein the cylindrical member includes a groove formed therein and extending from the proximal end to the distal end, and the slidable weight includes a protruding element extending into the groove.

36. The implant insertion tool of claim 34, wherein the distal end of the cylindrical member includes a locking element for locking the slidable weight in the first distal position.

37. The implant insertion tool of claim 36, wherein the locking element is an L-shaped groove extending radially around a portion of the cylindrical member, such that rotation of the slidable weight in the first distal position is effective to prevent movement of the slidable weight to the second proximal position.

38. The implant insertion tool of claim 35, wherein the groove includes a proximal end surface, and wherein movement of the slidable weight in a proximal direction is effective to cause the protruding element to abut the proximal end surface of the groove thereby creating a proximally directed force.

39. A medical device for inserting an implant between adjacent bone structures, comprising:
    a body defining a central axis and having a bore extending through the central axis;
    a pair of opposed levers pivotably mated to the body and extending distally from the body, the opposed levers being effective to separate adjacent bone structures;
    an elongate rod positioned between the opposed levers and being slidably disposed through the bore of the body, the elongate rod being adapted to insert an implant between adjacent bone structures; and
    a mass having an inner lumen formed therein and being slidably disposed around a portion of the body, the mass being movable between a distal position and a proximal position, wherein movement of the mass in a proximal direction is effective to generate a proximally directed force that is effective to move the body and the opposed levers proximally with respect to the elongate rod.

40. The device of claim 39, further comprising an engagement member disposed between the mass and the body, the engagement member being effective to limit movement of the mass with respect to the body.

41. The device of claim 40, wherein the engagement member comprises a groove formed on one of the body and the inner lumen of the mass, and a protruding member formed on the other one of the body and the inner lumen of the mass, the protruding member being slidably disposed within the groove.

42. The device of claim 41, further comprising a locking element disposed between the mass and the body, the locking element being effective to prevent movement of the mass with respect to the body.

* * * * *